United States Patent [19]
Zampino et al.
[11] Patent Number: 4,877,769
[45] Date of Patent: Oct. 31, 1989

[54] 6,7-(EPITHIO)-3,7-DIMETHYL-1,3-OCTADIENE AND USE THEREOF IN AUGMENTING OR ENHANCING AROMA OF PERFUME COMPOSITIONS, COLOGNES AND PERFURMED ARTICLES

[75] Inventors: Michael J. Zampino, Roselle Park; Richard A. Wilson, Westfield; Braja D. Mookherjee, Holmdel, all of N.J.; Jean C. Niel, New-Canaan, Conn.

[73] Assignee: International Flavors & Fragrances Inc., New York, N.Y.

[21] Appl. No.: 345,015

[22] Filed: Apr. 28, 1989

[51] Int. Cl.[4] .................... A61K 7/46
[52] U.S. Cl. .................... 512/11; 549/1; 252/174.11; 252/8.6; 512/4
[58] Field of Search .................... 512/11, 4; 252/174.11, 252/8.6; 549/1

[56] References Cited

U.S. PATENT DOCUMENTS

| | | | |
|---|---|---|---|
| 3,671,551 | 6/1972 | Bledsoe | 512/11 |
| 3,979,425 | 9/1976 | Buchi et al. | 512/11 |
| 4,388,228 | 6/1983 | Boden et al. | 512/11 |
| 4,536,583 | 8/1985 | Mookherjee et al. | 549/1 |

OTHER PUBLICATIONS

Suga et al, Chem. Abst., vol. 59, #11574e (1963).

*Primary Examiner*—James H. Reamer
*Attorney, Agent, or Firm*—Arthur L. Lieberman

[57] ABSTRACT

Described are the 6,7-(epithio)-3,7-dimethyl-1,3-octadienes having the structures

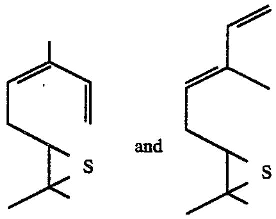

and mixtures of same as well as the uses thereof in augmenting or enhancing the aroma or perfume compositions, colognes and perfumed articles including but not limited to solid or liquid anionic, cationic, nonionic or zwitterionic detergents, cosmetic powders, hair preparations and the like.

9 Claims, 5 Drawing Sheets

GLC PROFILE FOR EXAMPLE I.

GC-MS SPECTRUM FOR EXAMPLE I.

GC-MS SPECTRUM FOR EXAMPLE I.

NMR SPECTRUM FOR EXAMPLE I.

6,7-(EPITHIO)-3,7-DIMETHYL-1,3-OCTADIENE AND USE THEREOF IN AUGMENTING OR ENHANCING AROMA OF PERFUME COMPOSITIONS, COLOGNES AND PERFURMED ARTICLES

BACKGROUND OF THE INVENTION

Our invention relates to 6,7-(epithio)-3,7-dimethyl-1,3-octadiene having the structures:

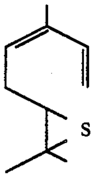

and

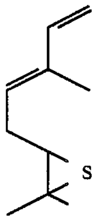

and mixtures thereof useful in augmenting or enhancing the aroma of perfume compositions, colognes and perfumed articles.

Chemical compounds which can provide natural stemmy and green aromas with basil and marigold undertones and neroli, tagette and petitgrain topnotes are highly desirable in the art of perfumery. Many of the natural materials which provide such fragrances and contribute such desired nuances to perfumery compositions are high in cost, unobtainable at times, vary in quality from one batch to another and/or are generally subject to the usual variations of natural products.

Epithio compounds are known as being useful as intermediates in preparing mercapto derivatives which are known to be useful for their organoleptic properties. Thus, the compound having the structure:

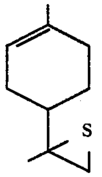

is known to be useful as an intermediate in preparing the compound having the structure:

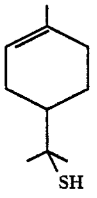

which is indicated to be useful for its organoleptic properties in U.S. letters Pat. No. 4,536,583 issued on Aug. 20, 1985. However, epithio derivatives per se are not known in the art of perfumery.

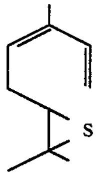

and

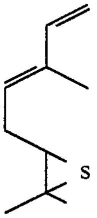

Figure 1:
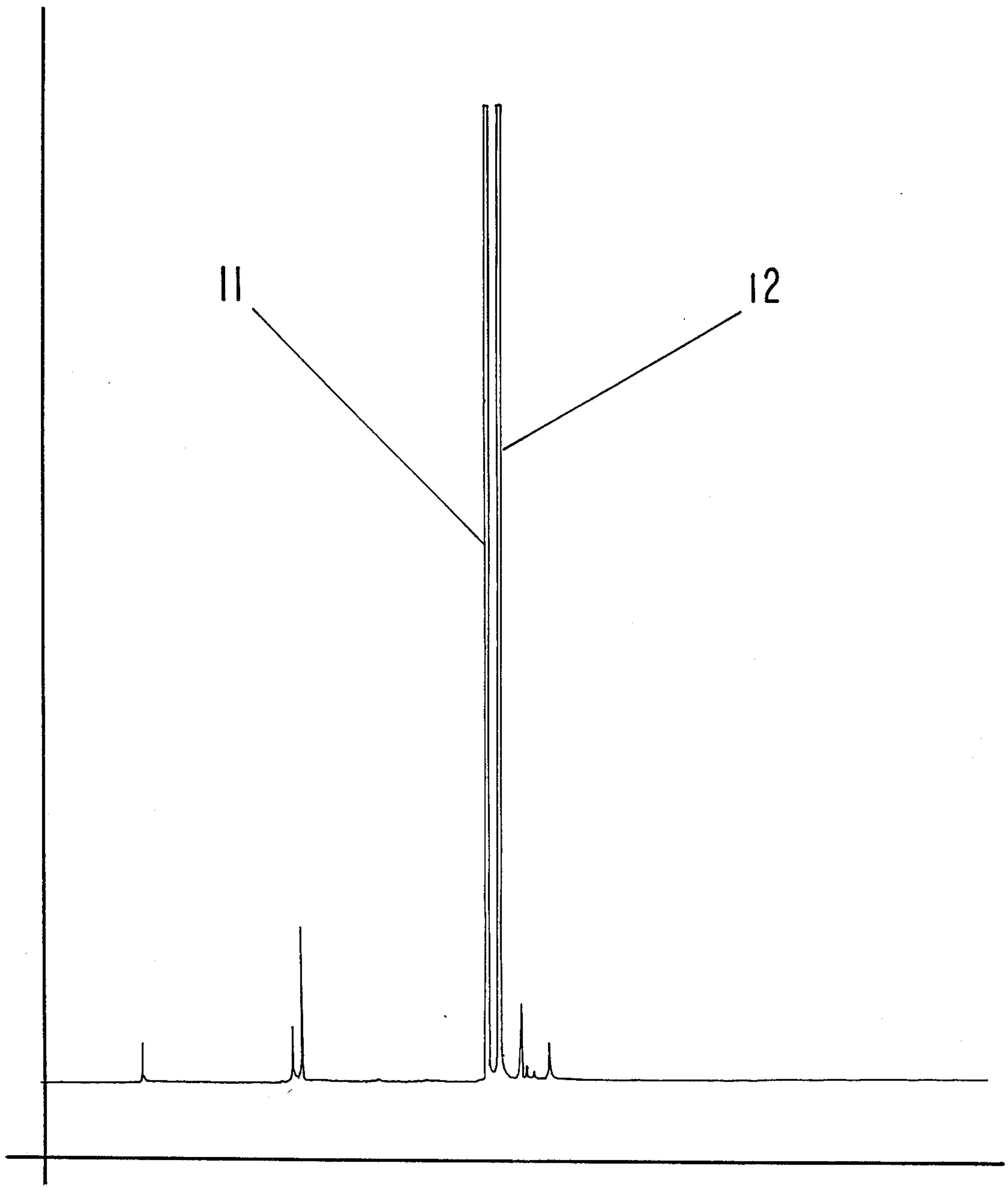
FIG. 1 is the GLC profile for fraction 5 of the distillation product of the reaction product of Example I containing the compounds having the structures.
Figure 2:
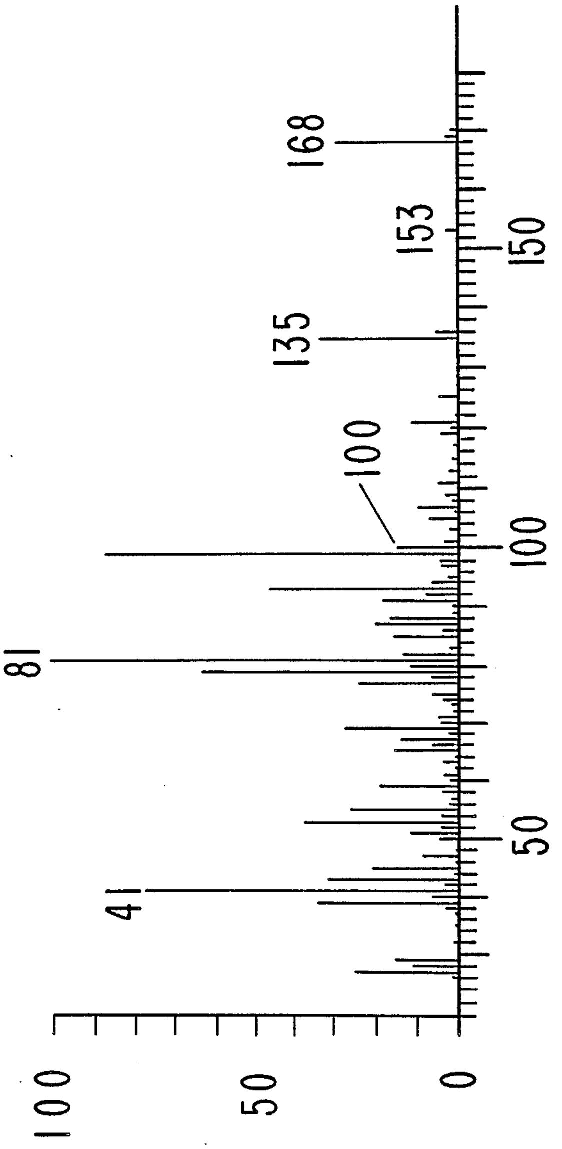

FIG. 2 is the GC-MS spectrum for the "E" isomer having the structure:

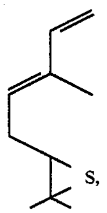

indicated by the peak having the reference numeral 12 on the GLC profile of FIG. 1.

Figure 3:
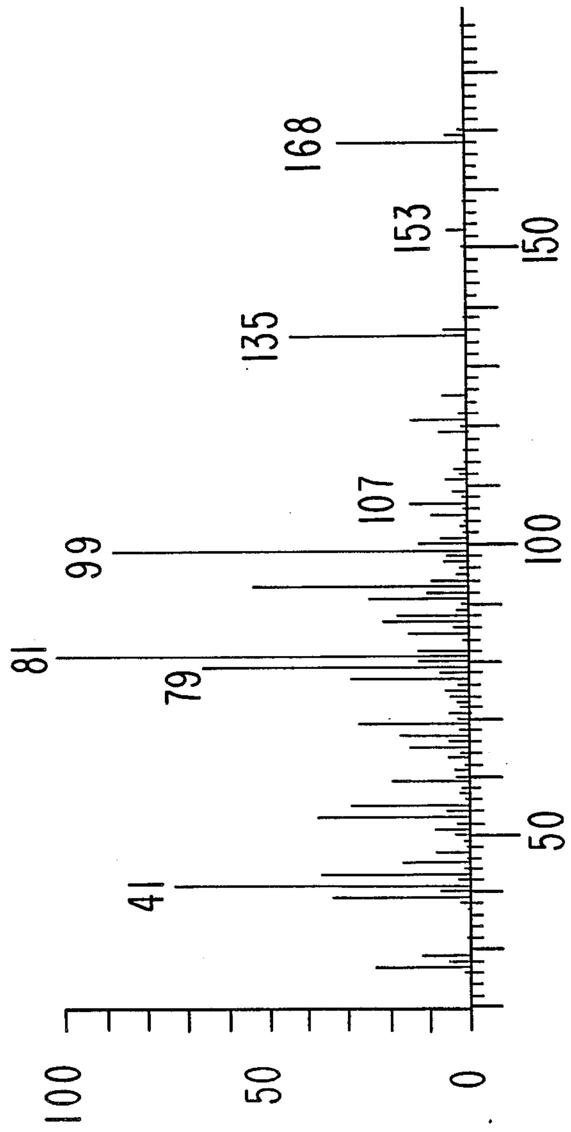

FIG. 3 is the GC-MS spectrum for the compound having the structure:

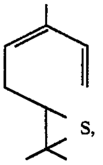

the "Z" isomer which is the peak indicated by reference numeral 11 in the GLC profile of FIG. 1.

Figure 4:
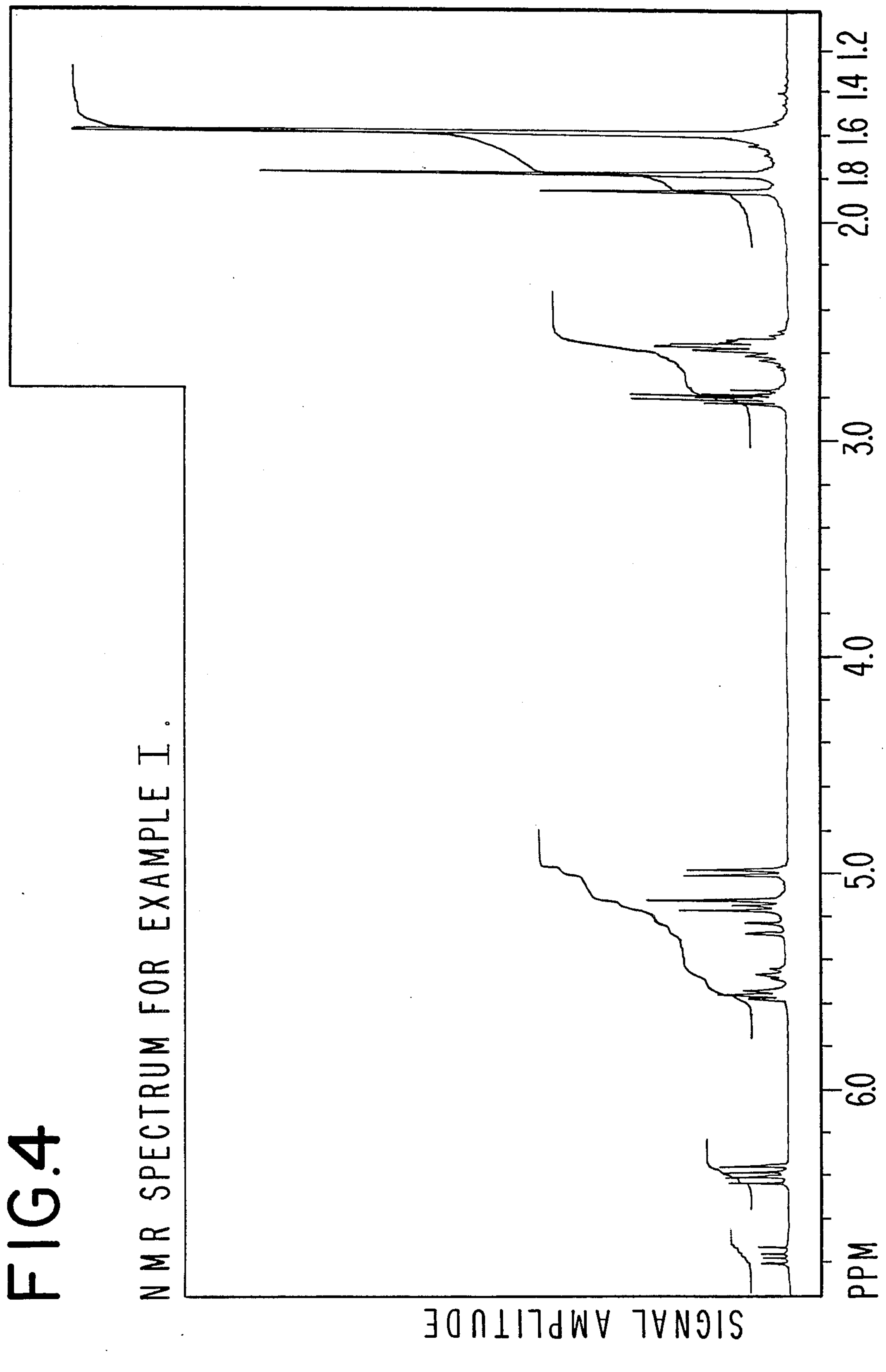

FIG. 4 is the NMR spectrum for the mixture of isomers having the structures:

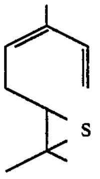

and

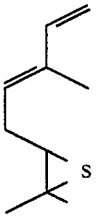

of fraction 5 of the distillation product of the reaction product of Example I.

Figure 5:
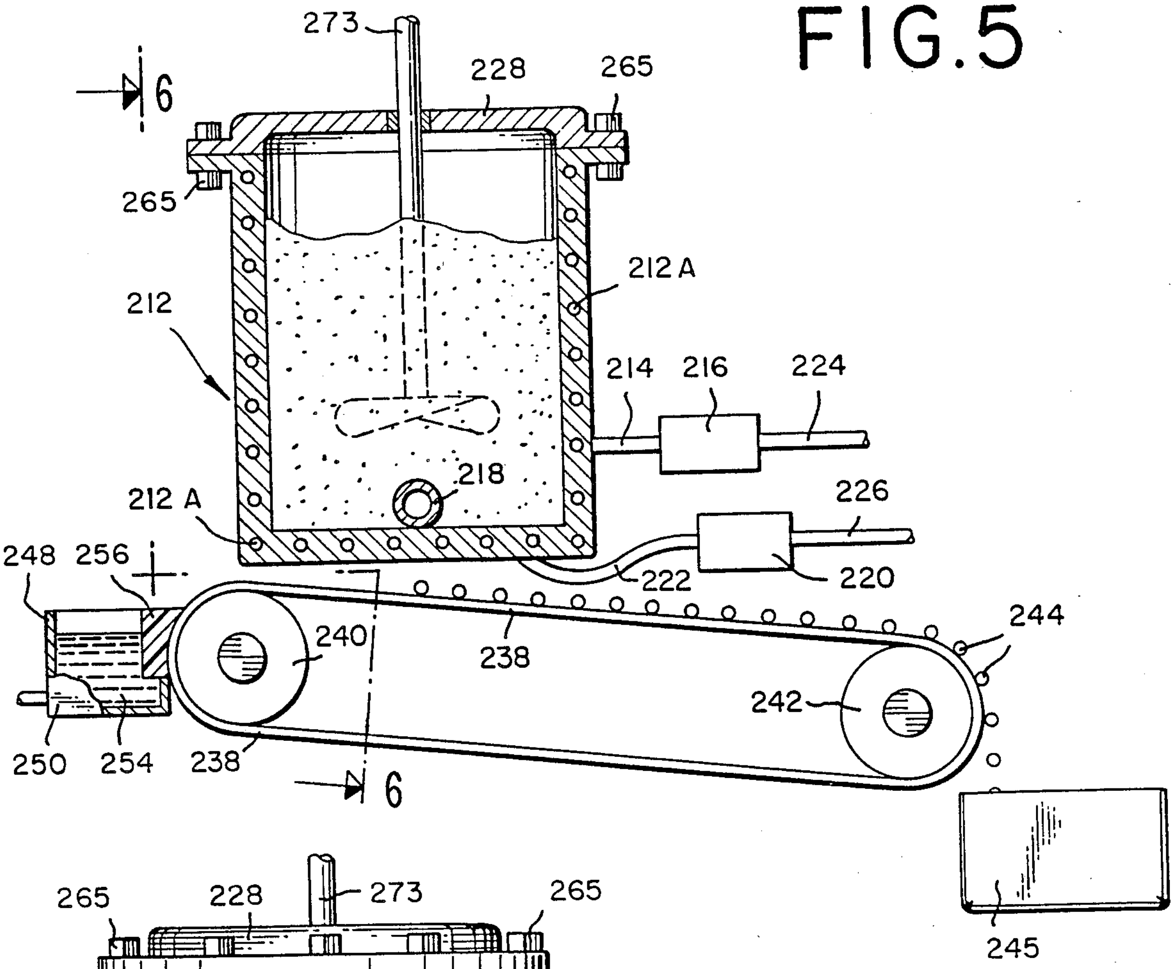

FIG. 5 is a partial side elevation and partial sectional view of an apparatus for forming scented polymer using the compounds having the structures:

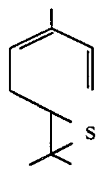
and/or
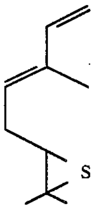

prepared according to Example I.

Figure 6:
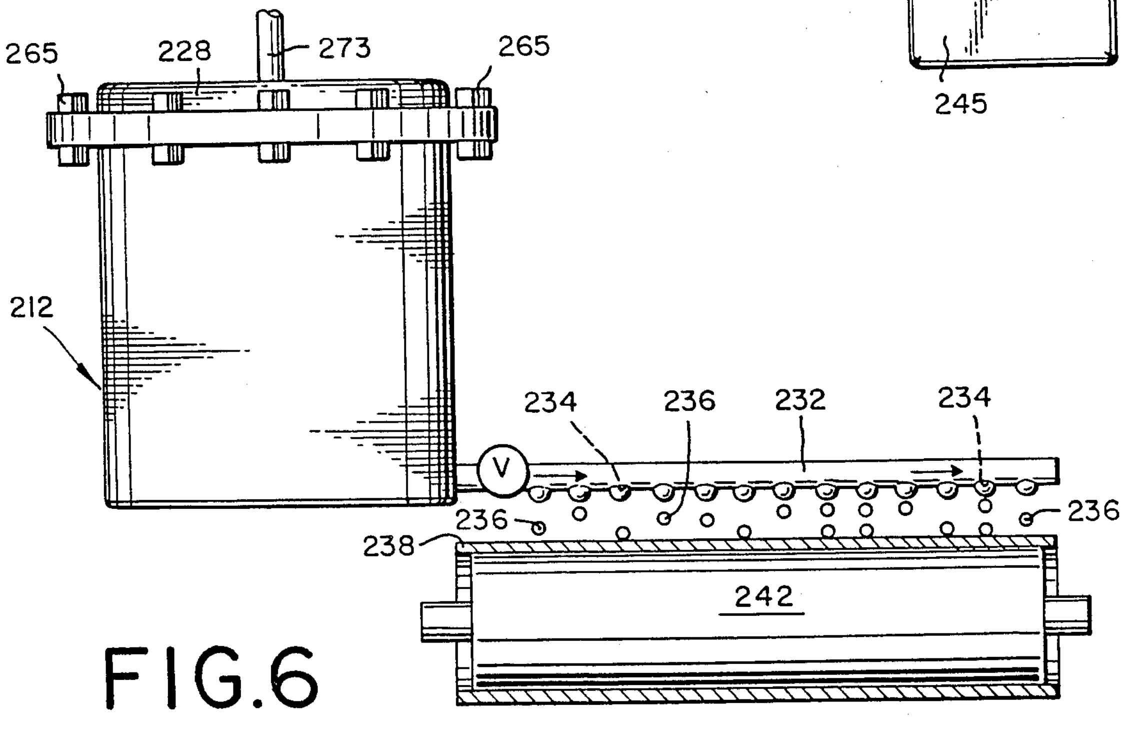

FIG. 6 is a section taken along line 6—6 of FIG. 5.

DETAILED DESCRIPTION OF THE DRAWINGS

FIG. 1 is the GLC profile for fraction 5 of the distillation product of the reaction product of Example I containing the isomers having the structures:

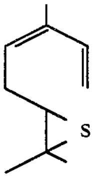
and
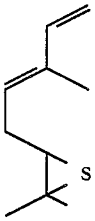

The peak indicated by reference numeral 11 is the peak for the "Z" isomer having the structure:

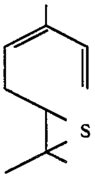

The peak indicated by reference numeral 12 is the peak for the "E" isomer having the structure:

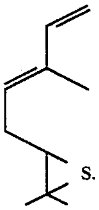

Referring to the drawings in FIGS. 5 and 6 in particular, the invention embodied therein comprises a device for forming scented polymer pellets (e.g., polyethylene, polypropylene or mixtures of polyepsilon caprolactone and polyethylene or polypropylene or co-polymers or polyvinyl acetate and polyethylene) which comprises a vat or container 210 into which a mixture of polymer such as polyethylene and one or more compounds defined according to the structures:

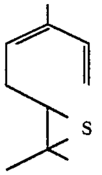
and/or
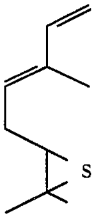

or a mixture of perfume materials including as a key ingredient one of the isomers defined according to the structures:

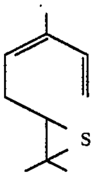
and/or
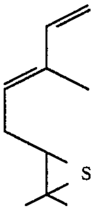

or a mixture of perfume materials including as a key ingredient one of the isomers defined according to one of the structures:

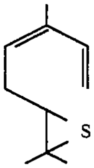
and/or
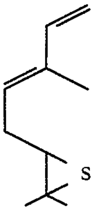

is placed.

The container is closed by an air-tight lid 228 clamped to the container by clamps 265. A stirrer 273 traverses the lid or cover 228 in air-tight manner and is rotated in suitable manner. A surrounding cylinder 212 having heating coils which are supplied with electrical current through cable 214 from a rheostat or control 216 is operated to maintain the temperature inside the container 210 such that the polymer such as polyethylene in the container will be maintained in a molten or liquid state. It has been found advantageous to employ a colorless, odorless polymer such as low density polyethylene with a viscosity ranging between 180 and 220 centistokes and having a melting point in the neighborhood of 220° F. The heater 212 is operated to maintain the upper portion of the container 210 within a temperature range of from 250°–350° F. An additional bottom heater 218 is regulated through a control 220 connected thereto through a connecting wire 222 to maintain the lower portion of the container 210 within a temperature range of from 250° to 350° F.

In accordance with this aspect of the invention, a polymer such as polyethylene or polypropylene is added to the container 210 and is then heated from 10 to 12 hours whereafter a scent or aroma-imparting material containing one or more of the isomers having the structures:

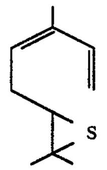
and/or
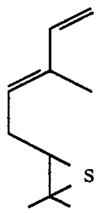

is quickly added to the melt. The material must be compatible with the polymer and forms a homogeneous liquid melt therewith. The heat resisting material, generally about 10–40% by weight of one or both of the 6,7-(epithio)-3,7-dimethyl-1,3-octadienes of our invention is added to the polymer.

After the above mixture of perfumery chemicals is added to container 210, the mixture is stirred for a few minutes, for example, 5 to 15 minutes, and maintained within the temperature range as indicated previously by the heating coils 212 and 218 respectively. The controls 216 and 220 are connected through cables 224 and 226 to a suitable supply of electric current for supplying the power for heating purposes.

Thereafter the valve "V" is opened permitting the mass to flow outwardly through a conduit 232 having a multiplicity of orifices 234 adjacent the lower side thereof. The outer end of the conduit 232 is closed so that the liquid polymer and perfumery chemical mixture will continuously drop through the orifices 234 downwardly from the conduit 232. During this time the temperature of the polymer and the perfumery chemical mixture in the container 210 is accurately controlled so that a temperature in the range of from 210° F. up to 275° F. will exist in the conduit 232. The regulation of the temperature through the control 216 and the control 220 is essential in order to insure temperature balance to provide for the continuous dropping or dripping of molten polymer and perfumery chemical mixture of our invention through the orifices 234 at a range which will insure the formation of droplets 236 which will fall downwardly onto a moving conveyor belt 238 trained to run between conveyor wheels 240 and 242 beneath the conduit 232. When droplets 236 fall onto the conveyor belt 238 they form pellets 244 which harden almost instantaneously and fall off the end of the conveyor 238 into a container 246 which is advantageously filled with water or some other suitable liquid to insure the rapid cooling of each of the pellets. The pellets 244 are then collected from the container 246 and packaged for shipment.

A feature of the invention is the provision for moistening the conveyor belt 238 to insure the rapid formation of the solid polymer scented pellets 244 without sticking to the belt. The belt 238 is advangtageously of a material which will not normally stick to a melted polymer but the moistening means 248 insures a sufficiently cold temperature of the belt surface for the adequate formation of the pellets 244. The moistening means comprises a container 250 which is continuously fed with water 252 to maintain a level 254 for moistening a sponge element 256 which bears against the exterior surface of the belt 238.

THE INVENTION

It has now been discovered that novel perfume compositions and perfumes as well as perfumed articles having extended long-lasting, natural stemmy, green aromas with basil and marigold undertones and neroli, tagette and petitgrain topnotes may be provided by the utilizaton of one or a mixture of the isomers having the structures:

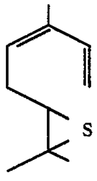
and
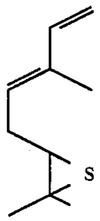

The compounds having the structures:

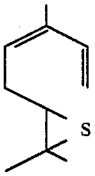
and
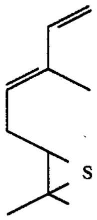

are known as 6,7-(epithio)-3,7-dimethyl-1,3-octadienes.

The 6,7-(epithio)-3,7-dimethyl-1,3-octadienes of our invention may be prepared by means of reacting one or both of the compounds having the structures:

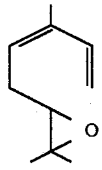
and/or
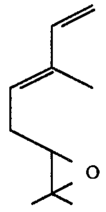

with an alkali metal thiocyanate having the structure:

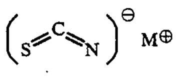

wherein M represents alkali metal such as sodium, potassium and lithium in accordance with the reaction:

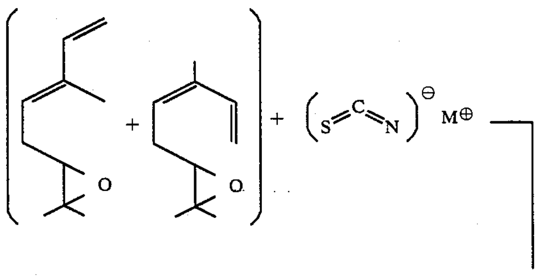

-continued

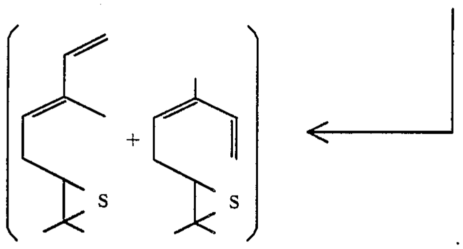

The resulting isomer or mixture of isomers having the structures:

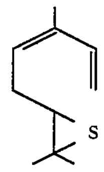

and/or

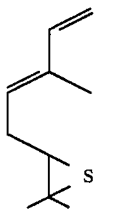

may then be fractionally distilled under vacuum and the resulting product may then be used as is or in the event of a mixture of isomers having the structures:

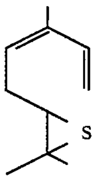

and

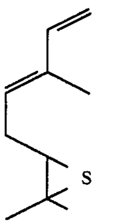

the mixture may be separated into its respective isomeric components using preparative column chromatography.

In the foregoing reaction, the mole ratio of alkali metal thiocyanate:epoxide isomers having one or both of the structures:

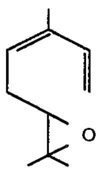

and/or

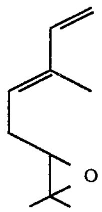

may vary from about 8:1 down to about 1:1 with a preferred mole ratio of alkali metal thiocyanate:epoxide being about 4:1. The reaction takes place in a two phase system with the alkali metal thiocyanate being dissolved in water (e.g., between 10% and 50% solution of alkali metal thiocyanate in water). The reaction may take place using an additional solvent, e.g., isopropyl alcohol or it may take place in the presence of a phase transfer agent such as ALIQUAT ®336 (for example) manufactured by the Henkel Chemical Company of Minneapolis, Minn. ALIQUAT ®336 is tricaprylmethyl ammonium chloride.

Thus, one aspect of our invention involving the process covered by the reaction:

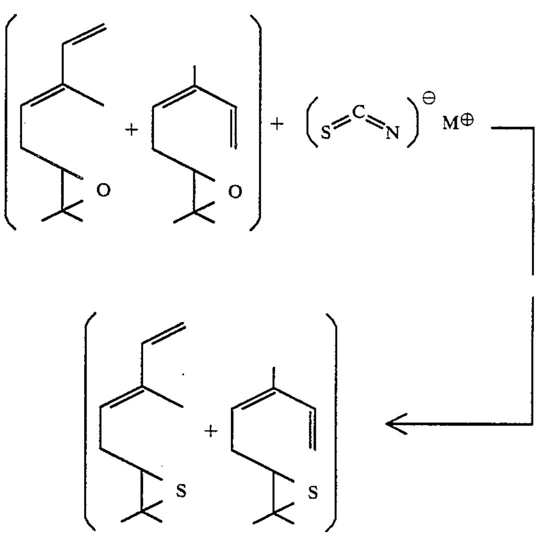

comprises the step of placing the reactants of the process in two immiscible phases, an organic phase and an aqueous alkali metal thiocyanate phase and adding to this two-phase system a "phrase transfer agent" which may be one or more of several organic quaternary ammonium salts as mentioned, supra.

Specific examples of phase transfer agents useful in our invention are as follows:

tricapryl methyl ammonium chloride;
cetyl trimethyl ammonium chloride;
cetyl trimethyl ammonium bromide; and
benzyl trimethyl ammonium hydroxide.

In general, the phase transfer agents most preferred have the generic formula:

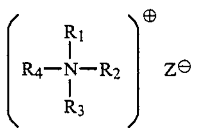

wherein at least one of $R_1$, $R_2$, $R_3$ and $R_4$ is $C_6$–$C_{14}$ aryl, $C_6$–$C_{10}$ aralkyl, $C_6$–$C_{20}$ alkyl, $C_6$–$C_{14}$ alkaryl and $C_6$–$C_{20}$ alkenyl and the other of $R_2$, $R_3$ and $R_4$ is alkyl such as methyl, ethyl, n-propyl, i-propyl, 1-butyl, 2-butyl, 1-methyl-2-propyl, 1-pentyl and 1-octyl and Z is an anion such as chloride, bromide and hydroxide.

Whether a phase transfer agent is used or not, the reaction temperature may vary from about 55° C. up to about 100° C. and the pressure may vary from about 1 atmosphere up to about 10 atmosphere with a preferred reaction temperature being between about 75° C. and about 95° C. and a preferred and convenient reaction pressure being 1 atmosphere.

At the end of the reaction, the reaction mass is separated and the organic phase is extracted with an inert extraction material, e.g., methylene dichloride ($CH_2Cl_2$). The extract is evaporated and the resulting extract is then fractionally distilled in vacuum to yield in the usual case the mixture of isomers having the structures:

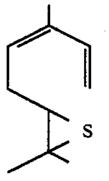
and
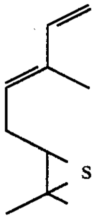

since from a practical standpoint the starting material is a mixture of isomers having the structure:

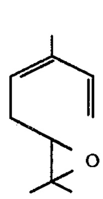
and
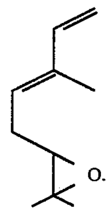

The resulting isomer mixture having the structures:

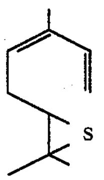
and
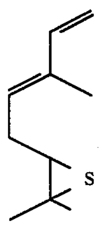

may at this point in time be separated using preparative chromatographic techniques.

As an example, the mixture of isomers having the structures:

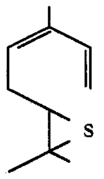
and
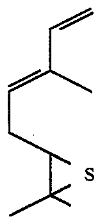

distills at a vapor temperature of about 80° C. and a liquid temperature of about 100° C. at a vacuum of 2.10 mm/Hg. pressure.

When the 6,7-(epithio)-3,7-dimethyl-1,3-octadienes of our invention are used as perfume aroma adjuvants, the nature of the co-ingredients included with said 6,7-(epithio)-3,7-dimethyl-1,3-octadienes in formulating the product composition will also serve to alter the organoleptic characteristics of any ultimate perfumed article treated therewith.

As used herein the terms "alter" and "modify" in their various forms means supplying or imparting a perfume aroma character or note to otherwise bland substances or augmenting the existing aroma characteristics where natural aroma is deficient in some regard or supplementing the existing aroma impression to modify its quality, character or aroma.

As used herein the term "enhance" is intended to mean the intensification (without effecting a change in kind or quality of aroma) of one or more aroma nuances and their organoleptic impression of a perfume, perfume composition or one or more perfumed articles.

The 6,7-(epithio)-3,7-dimethyl-1,3-octadienes of our invention and one or more auxiliary perfume ingredients including, for example, alcohols, aldehydes, ketones, nitriles, esters, lactones, natural essential oils, synthetic essential oils and mercaptans may be admixed so that the combined odors of the individual components produce a pleasant and desired fragrance, particularly and preferably in the marigold, rose, iris and hyacinth fragrance area.

It is to be understood that such additional adjuvants are to be organoleptically compatible with each of the 6,7-(epithio)-3,7-dimethyl-1,3-octadienes of our invention and further that such adjuvants are to be non-reactive under use conditions at room temperature and storage conditions with the 6,7-(epithio)-3,7-dimethyl-1,3-octadienes of our invention.

Such perfume compositions usually contain (a) the main note or bouquet or foundation stone of the compositions; (b) modifiers which round off and accompany the main note; (c) fixatives which include odorous substances which lend a particular note to the perfume throughout all stages of evaporation and substances which retard evaporation; and (d) topnotes which are usually low-boiling, fresh-smelling materials.

It is the individual components which will contribute their particular olfactory characteristics; and these individual components will also alter, modify or enhance the overall effect of the perfume composition. Thus, the 6,7-(epithio)-3,7-dimethyl-1,3-octadiene of our invention can be used to alter, augment or enhance the aroma characteristics of a perfume composition, for example, by utilizing or moderating the olfactory reaction contributed by one or more other ingredients in the composition.

The amount of 6,7-(epithio)-3,7-dimethyl-1,3-octadiene of our invention which will be effective in the perfume composition depends on many factors including the other ingredients, their amounts and the effects which are desired.

It has been found that perfume compositions containing as little as $10^{-4}\%$ of the 6,7-(epithio)-3,7-dimethyl-1,3-octadienes of our invention can be used to impart intense and long-lasting, natural stemmy and green aromas with basil and marigold undertones and neroli, tagette and petitgrain topnotes to cosmetics and other products including fabric softener articles used in clothes driers, solid or liquid anionic, cationic, nonionic or zwitterionic detergents and perfumed polymers. The amount employed can range up to 10% of the fragrance components and will depend on considerations of cost, nature of the end product, the effect desired on the finished product and the particular fragrance sought.

The 6,7-(epithio)-3,7-dimethyl-1,3-octadienes of our invention are useful taken alone or in perfume compositions as an olfactory component in anionic, cationic, noninic or zwitterionic detergents and soaps, space odorants and deodorants, perfumes, colognes, toilet water, bath preparations such as bath oils and bath solids, hair preparations such as lacquers, brilliantines, pomades and shampoos; cosmetic preparations such as creams, deodorants, hand lotions and sun screens; powders such as talcs, dusting powders and face powders; perfumed polymers; insect repellents; animal repellents; and insect and animal pheremones.

When used as an olfactory component in a perfumed article (e.g., detergent), as little as 0.0025% of one or both of the 6,7-(epithio)-3,7-dimethyl-1,3-octadienes of our invention will suffice to impart a natural stemmy green aroma with basil and marigold undertones and neroli, tagette and petitgrain topnotes thereto. Generally no more than 3% of one or both of the 6,7-(epithio)-3,7-dimethyl-1,3-octadienes of our invention based on the ultimate end product is required in the perfumed article. Accordingly, the range of one or both of the 6,7-(epithio)-3,7-dimethyl-1,3-octadienes of our invention in the perfumed article may vary from about 0.0025% up to about 3% by weight of the perfumed article.

In addition, the perfume composition or fragrance composition of our invention can contain a vehicle or carrier for one or both of the 6,7-(epithio)-3,7-dimethyl-1,3-octadienes of our invention. The vehicle can be a liquid such as a non-toxic alcohol (e.g., 95% food grade ethanol), a non-toxic glycol (e.g., propylene glycol) or the like. The carrier can also be an absorbent solid such as a gum (e.g., gum arabic, xanthan gum or guar gum or mixtures of same) or components for encapsulating the composition (such as gelatin as by means of coacervation) or such as urea-formaldehyde prepolymer for formulation of the urea-formaldehyde polymer around a liquid perfume center.

More specifically, one or both of the 6,7-(epithio)-3,7-dimethyl-1,3-octadienes of our invention may be blended into polymers when forming a perfumed polymer by means of extrusion using a single or double screw extruder or technique such as that set forth in U.S. Pat. No. 4,247,498 issued on Jan. 27, 1981 (the specification for which is incorporated herein by reference) which discloses microporous polymers which are capable of containing volatile substances such as perfumes and the like in forms ranging from films to blocks and intricate shapes from synthetic thermoplastic polymers such as olefinic, condensation or oxidation polymers.

Other techniques of blending one or both of the 6,7-(epithio)-3,7-dimethyl-1,3-octadienes of our invention with polymers are exemplified in U.S. Pat. No. 3,505,432 (the specification for which is incorporated herein by reference) which discloses a method for scenting a polyolefin with such materials as one or both of the 6,7-(epithio)-3,7-dimethyl-1,3-octadienes of our invention which process comprises:

(a) mixing a first amount of the liquid polyolefin (e.g., polyethylene or polypropylene) with a relatively large amount of scent-imparting material (in this case one or both of the 6,7-(epithio)-3,7-dimethyl-1,3-octadienes of our invention) to form a flowable mass;

(b) forming drops of said mass and causing substantially instantaneous solidification of said drops into polyolefin pellets having a relatively large amount of such scent-imparting materials as one or both of the 6,7-(epithio)-3,7-dimethyl-1,3-octadienes of our invention imprisoned therein;

(c) melting said pellets with a second amount of polyolefin with said second amount being larger than said first amount; and (d) solidifying the melt of (c).

As stated, supra, a key constituent of the perfume composition of our invention is one of the 6,7-(epithio)-3,7-dimethyl-1,3-octadienes defined according to the structures:

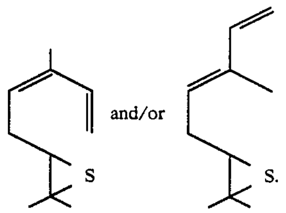

It will thus, be apparent that one or both of the 6,7-(epithio)-3,7-dimethyl-1,3-octadienes of our invention can be utilized to alter, modify, augment or enhance sensory properties, particularly organoleptic properties such as fragrances.

The following Example I serves to illustrate a method for preparing one or both of the 6,7-(epithio)-3,7-dimethyl-1,3-octadiene of our invention. The following Examples II, et seq, serve to illustrate the organoleptic utilities of one or both of the 6,7-(epithio)-3,7-dimethyl-1,3-octadienes of our invention. This invention is to be considered restricted to the examples only as indicated in the appended claims.

All parts and percentages given herein are by weight unless otherwise specified.

EXAMPLE I

Preparation of 6,7-(Epithio)-3,7-Dimethyl-1,3-Octadiene

Reaction

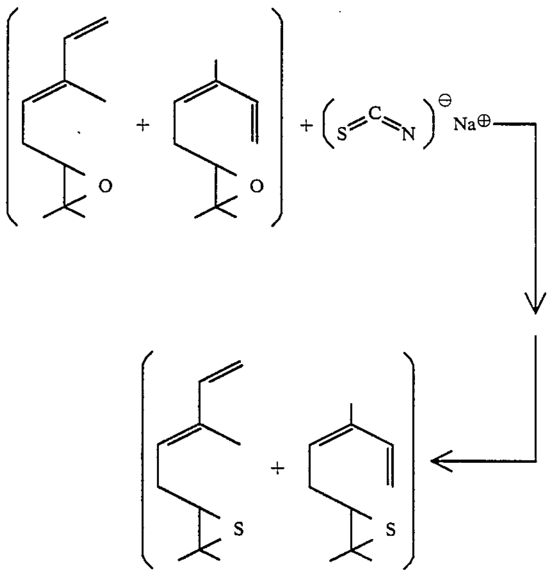

Into a 2 liter reaction flask equipped with condenser, stirrer, thermometer and heating mantle is placed 550 ml isopropyl alcohol; 550 ml water; and 400 grams (4.94 moles) of sodium thiocyanate.

With stirring the solid dissolves.

280 Grams (1.84 moles) of the mixture of isomers having the structures:

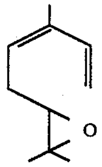
and
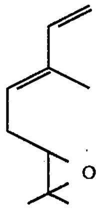

is then added to the reaction mass.

Over a period of 8.5 hours the reaction mass is heated at reflux at 87° C.

At the end of the 8.5 hour period, the reaction mass is cooled to room temperature and poured into 800 ml water. 800 ml Methylene dichloride is added to the reaction mass. The reaction mass now exists in two phases; an organic phase and an aqueous phase.

The aqueous phase is extracted with 30 ml methylene dichloride. The extract is bulked with the organic phase and the bulked organic phase is washed with three volumes of saturated sodium chloride solution.

The organic phase is then concentrated on a rotovap evaporator.

The resulting product is then distilled on an one plate column at 110° C. vapor temperature and 160° C. liquid temperature at a 1.8 mm/Hg. vacuum. The resulting distillate is then redistilled on a one foot silver mirror column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 54/ | 84/ | 1.07 | 1:4 | 14.3 |
| 2 | 67 | 85 | 1.02 | 4:1 | 18.4 |
| 3 | 50 | 85 | 2.44 | 9:1 | 5.7 |
| 4 | 80 | 96 | 2.10 | 9:1 | 6.0 |
| 5 | 80 | 100 | 2.10 | 9:1 | 10.1 |
| 6 | 78 | 105 | 2.0 | 25/15 | 8.0 |
| 7 | 60 | 120 | 1.6 | | 6.0. |

FIG. 1 is the GLC profile for fraction 5 of the foregoing distillation. The peak indicated by reference numeral 11 is the peak for the "Z" isomer having the structure:

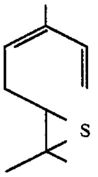

The peak indicated by reference numeral 12 is the peak for the "E" isomer having the structure:

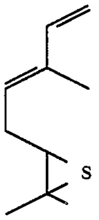

FIG. 2 is the GC-MS spectrum for the "E" isomer (peak 12 of FIG. 1) having the structure:

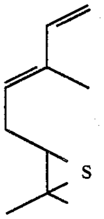

FIG. 3 is the GC-MS spectrum for the "Z" isomer having the structure:

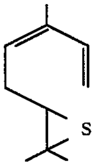

(peak 11 on FIG. 1).

FIG. 4 is the NMR spectrum for fraction 5 containing the mixture of isomers having the structures:

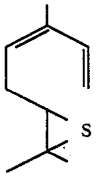
and
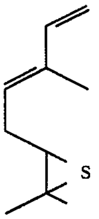

Fraction 5 has a natural stemmy, green aroma with basil and marigold undertones and neroli, tagette and petitgrain topnotes.

EXAMPLE II

Preparation of Rose/Marigold Formulation

The following mixture is prepared:

| Ingredients | Parts by Weight |
|---|---|
| Rhodinol | 270.0 |
| Nerol | 90.0 |
| Linalool | 30.0 |
| Terpineol | 30.0 |
| Phenyl Ethyl Alcohol | 12.0 |
| Terpinenol | 5.0 |
| Linalyl acetate | 1.5 |
| Citronellyl acetate | 15.0 |
| Geranyl acetate | 10.0 |

-continued

| Ingredients | Parts by Weight |
|---|---|
| Eugenol | 33.0 |
| Citral | 15.0 |
| Phenyl Ethyl Acetate | 20.0 |
| Rose oxide | 8.0 |
| Guaiacol | 30.0 |
| 1-citronellal | 90.0 |
| Neryl acetate | 3.0 |
| Clove bud oil | 1.0 |
| Cadinene | 2.0 |
| Guaiene | 1.0 |
| Gum turpentine | 12.0 |
| Alpha-pinene | 1.0 |
| Myrcene | 5.0 |
| Limonene | 2.0 |
| p-cymene | 1.0 |
| The mixture of isomers having the structure: 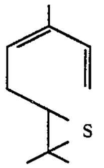 and 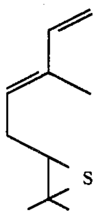 prepared according to Example I, distillation fraction 5. | 18.0 |

The resultant mixture has a rose and marigold aroma profile with natural stemmy, green and basil undertones and neroli, tagette and petitgrain topnotes.

EXAMPLE III

Preparation of a Soap Composition

One hundred grams of soap chips are prepared according to Example V of U.S. Pat. No. 4,058,490 issued on Nov. 15, 1977 as follows:

"The sodium salt of an equal mixture of $C_{10}/C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the reamining aqueous solution is drum dried. The resulting solid actives are then blended in a chip mixer wit 10 lbs. water, 0.2 lbs. titanium hydroxide"

and mixed with one gram of the perfume composition of Example II until a substantally homogeneous composition is obtained. The perfumed soap composition manifests an excellent rose and marigold character with stemmy, green and basil undertones and neroli, tagette and petitgrain topnotes.

EXAMPLE IV

Preparation of a Detergent Composition

A total of 100 grams of detergent powder prepared according to U.S. Pat. No. 4,058,472 and containing 5% by weight of the sodium salts of a mixture of sulfonated $C_{14}$–$C_{18}$ alkyl catechol as a surface active component, the mixture being 60 parts by weight of mono-$C_{14}0C_{18}$ alkyl catechol, 35% sodium tetrapyrrole phosphate, 30% of sodium carboxymethylcellulose and 7% of starch is mixed with 0.15 grams of the perfume composition of Example II until a substantially homogeneous composition is obtained. This composition has an excellent rose and marigold aroma with basil, natural stemmy and green undertones and neroli, tagette and petitgrain topnotes.

EXAMPLE V

Perfumed Liquid Detergent

Concentrated liquid detergents each with rose, marigold aromas and basil, natural stemmy and green undertones and neroli, tagette and petitgrain topnotes are prepared containing 0.10%, 0.15%, 0.20% and 0.25% of the mixture of compounds having the structures:

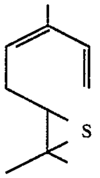
and
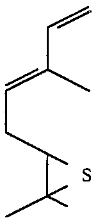

(which mixture is prepared according to Example I) in an amount of 0.0001%. They are prepared by adding and homogeneously mixing the appropriate quantity of mixture of compounds having the structures:

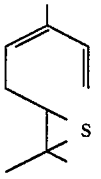
and
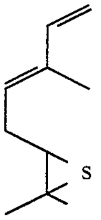

The detergents all possess rose and marigold aromas with basil, natural stemmy and green undertones and neroli, tagette and petitgrain topnotes, the intensity increasing with greater concentrations of mixture of compounds having the structures:

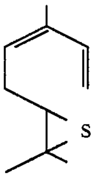
and
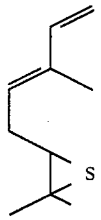

EXAMPLE VI

Preparation of Cologne and Handkerchief Perfume

The composition of Example II is incorporated in colognes at concentrations of 1.5%, 2.0%, 2.5%, 3.0% and 3.5% in 75%, 80%, 85% and 90aqueous ethanol; and into handkerchief perfumes at concentrations of 15%, 20% and 25% (in 85%, 90% and 95% aqueous ethanol). The use of the compounds having the structures:

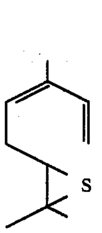

and

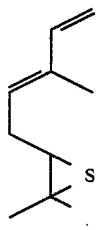

produced according to Example I affords distinct and strong natural stemmy and green aromas with basil and marigold undertones and neroli, tagette and petitgrain topnotes to the handkerchief perfume and to the cologne.

EXAMPLE VII

Utilizing the procedure of Example I at column 15 of U.S. Pat. No. 3,632,396 (the specification of which is incorporated herein by reference), a nonwoven cloth substrate useful as a drier-added fabric softening article of manufacture is prepared wherein the substrate, the substrate coating and the outer coating and the perfuming material are as follows:

1. a water "dissolvable" paper ("Dissolvo Paper");
2. Adogen 448 (melting point 140° F.) as the substrate coating; and
3. an outer coating having the following formulation (melting point about 150° F.):
   57% $C_{20-22}$HAPS
   22% isopropyl alcohol
   20% antistatic agent
   1% of a mixture of compounds having the structures:

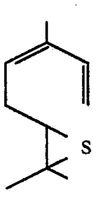

and

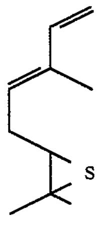

(giving rise to a natural stemmy, green aroma with basil and marigold undertones and neroli, tagette and petitgrain topnotes).

Fabric softening compositions prepared as set forth above having the above aroma characteristics essentially consist of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The resulting aroma can be described as natural stemmy and green with basil and marigold undertones and neroli, tagette and petitgrain topnotes. This aroma is imparted to the head space in the drier on operation thereof using the said drier-added fabric softening nonwoven fabric.

EXAMPLE VIII

Scented polyethylene pellets having a pronounced rose, marigold aroma with basil, natural stemmy and green undertones and neroli, tagette and petitgrain topnotes are prepared as follows:

Seventy-five pounds of polyethylene of a melting point of about 220° F. are heated to about 230° F. in a container of the kind illustrated in FIGS. 5 and 6. Twenty-five pounds of the perfume material of Example II is then added quickly to the liquified polyethylene. The lid 228 is put in place and the agitating means 273 are actuated. The temperature is maintained at about 225° F. and the mixing is then continued for about 5–15 minutes. The valve 230 is then opened to allow flow of the molten polyethylene enriched with the perfume composition of Example II-containing material to exit through the orifices 234. The liquid falling through the orifices 234 solidifies almost instantaneously upon impact with the moving, cooled conveyor 238. Solid polyethylene beads or pellets 244 having an aroma which can be described as rose-marigold with natural stemmy, green and basil undertones and neroli, tagette and petitgrain topnotes are then formed. Analysis demonstrates that the pellets contain about 25% of the perfume composition of Example II so that almost no losses of the scenting substance occur. These pellets may be called master pellets.

Fifty pounds of the scent-containing master pellets are then added to 1,000 pounds of unscented polyethylene powder and the mass is heated to the liquid state. The liquid is then molded into thin sheets or films. The sheets or films have pronounced rose-marigold aromas with basil natural stemmy and green undertones and neroli, tagette and petitgrain topnotes. The sheets are then also fabricated into garbage bags which have such an aroma.

What is claimed is:

1. An 6,7-(epithio)-3,7-dimethyl-1,3-octadiene selected from the group consisting of compounds having the structures:

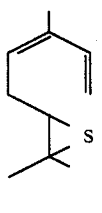

and

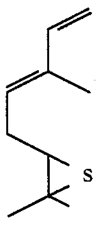

2. The 6,7-(epithio)-3,7-dimethyl-1,3-octadiene of claim 1 having the structure:

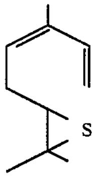

3. The 6,7-(epithio)-3,7-dimethyl-1,3-octadiene of claim 1 having the structure:

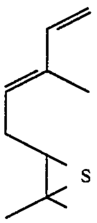

4. A process for augmenting or enhancing the aroma of a perfume composition, cologne or perfumed article comprising the step of adding to a perfume composition base, a cologne base or a perfumed article base, an aroma augmenting or enhancing quantity of at least one compound defined according to claim 1.

5. The process of claim 4 comprising the step of adding a mixture of compounds having the structures:

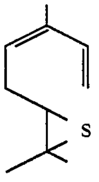
and
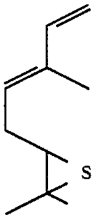

to a solid or liquid anionic, cationic, nonionic or zwitterionic detergent.

6. The process of claim 4 comprising the step of adding a mixture of compounds having the structures:

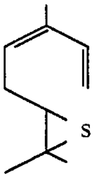
and
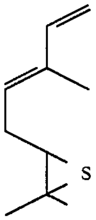

to a fabric softener composition.

7. The process of claim 4 comprising the step of adding to alcohol, a mixture of compounds having the structures:

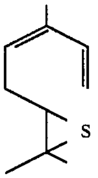
and
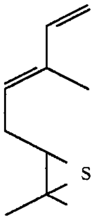

thereby forming a cologne.

8. A perfume composition comprising a perfume base and intimately admixed therewith, an aroma augmenting or enhancing quantity of a mixture of compounds having the structures:

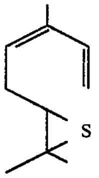
and
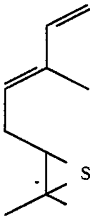

9. A perfume polymer comprising a polymer compatible with a compound selected from the group consisting of:

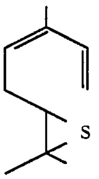
and
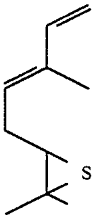

and intimately admixed therewith at least one compound defined according to claim 1.

* * * * *